United States Patent
Kato et al.

(10) Patent No.: US 9,131,894 B2
(45) Date of Patent: Sep. 15, 2015

(54) BIOLOGICAL INFORMATION DETECTING DEVICE

(71) Applicant: Seiko Instruments Inc., Chiba-shi, Chiba (JP)

(72) Inventors: Teruo Kato, Chiba (JP); Hideki Okuda, Chiba (JP); Dai Terasawa, Chiba (JP); Takahiro Kaneko, Chiba (JP)

(73) Assignee: SEIKO INSTRUMENTS INC., Chiba (JP)

( * ) Notice: Subject to any disclaimer, the term of this patent is extended or adjusted under 35 U.S.C. 154(b) by 0 days.

(21) Appl. No.: 14/518,394

(22) Filed: Oct. 20, 2014

(65) Prior Publication Data

US 2015/0119678 A1 Apr. 30, 2015

(30) Foreign Application Priority Data

Oct. 25, 2013 (JP) ................. 2013-222228

(51) Int. Cl.
*A61B 5/0408* (2006.01)
*A61B 5/00* (2006.01)
*A61B 5/024* (2006.01)
*A61B 5/04* (2006.01)

(52) U.S. Cl.
CPC .......... *A61B 5/6831* (2013.01); *A61B 5/02438* (2013.01); *A61B 5/04* (2013.01); *A61B 5/0408* (2013.01); *A61B 5/6823* (2013.01)

(58) Field of Classification Search
CPC . A61B 5/0408; A61B 5/04085; A61B 5/6831
USPC ......................................... 600/390
See application file for complete search history.

(56) References Cited

U.S. PATENT DOCUMENTS

| 7,167,737 B2 * | 1/2007 | Fujii et al. ............. 600/390 |
| 2013/0096411 A1 * | 4/2013 | Kato et al. ............. 600/390 |
| 2014/0094677 A1 * | 4/2014 | Okuda et al. ........... 600/390 |

FOREIGN PATENT DOCUMENTS

| DE | 20 2012 100 735 U1 | 7/2013 |
| EP | 1 559 365 A1 | 8/2005 |
| EP | 2 055 231 A1 | 5/2009 |
| GB | 2 291 505 A | 1/1996 |
| JP | 4439856 B2 | 3/2010 |

OTHER PUBLICATIONS

Extended European Search Report in corresponding European Application No. 14189074.9, dated Mar. 20, 2015, 6 pages.

* cited by examiner

*Primary Examiner* — Lee S Cohen
(74) *Attorney, Agent, or Firm* — Brinks Gilson & Lione

(57) ABSTRACT

Provision of a biological information detecting device capable of stably detecting a biological signal in good condition. A device body, a pair of electrode portions 26A and 26B provided in the device body and respectively contacting a biological surface and a band-shaped fixing band 30 for covering the pair of electrode portions 26A and 26B and fixing the device body to a body are provided, and a guide portion 40A which allows relative movement between each of the electrode portions 26A/26B and the fixing band 30 in an extending direction of the fixing band 30 and restricts movement in a width direction orthogonal to the extending direction is arranged between each of the electrode portions 26A/26B and the fixing band 30.

5 Claims, 10 Drawing Sheets

BIOLOGICAL INFORMATION DETECTING DEVICE

RELATED APPLICATIONS

This application claims priority under 35 U.S.C. §119 to Japanese Patent Application No. 2013-222228 filed on Oct. 25, 2013, the entire content of which is hereby incorporated by reference.

BACKGROUND OF THE INVENTION

1. Field of the Invention

The present invention relates to a biological information detecting device.

2. Description of the Related Art

There exist biological information detecting devices detecting a biological signal by allowing a sensor electrode to contact a biological surface. In this kind of biological information detecting devices, there is the one which measures a heart rate from the biological surface, for example, by detecting an electrocardiographic signal generated by heartbeats by the sensor electrode. As such biological information detecting device, there is the one including a pair of electrode portions and a device body transmitting an electrocardiographic signal detected by the electrode portions to the outside as disclosed in Japanese Patent No. 4439856 (Patent Literature 1). The device body is electrically connected to the pair of respective electrode portions by wires. Each of the pair of electrode portions includes a hook for holding the electrode portions at prescribed sites of the body by sandwiching a garment or the like mounted to a body. Then, the pair of electrode portions are pressed toward the biological surface by the garment and so on.

There is also disclosed a structure in which an attachment belt for holding the electrode portions at prescribed sites of the body is separately prepared instead of the garment and so on in Patent Literature 1 described below. In the attachment belt, a cut for receiving the hook is formed, which prevents displacement of positions of the electrode portions with respect to the attachment belt.

The heart rate is measured by detecting the electrocardiographic signal generated by heartbeats by the pair of electrode portions under the above structure.

However, in the case where the electrode portions are held by sandwiching the garment or the like by the hook in the above related art, it is difficult to obtain sufficient holding force with respect to the electrode portions only by sandwiching force of the hook. Accordingly, there are problems that pressing force of the electrode portions onto the biological surface is reduced when the electrode portions are displaced or removed from the garment or the like due to a moving manner of a wearer, which may hinder good detection of an electrocardiographic signal.

On the other hand, when the electrode portions are held by inserting the hook into the cut in the attachment belt or the like, the pressing force of the electrode portions onto the biological surface is not reduced as the positions of the electrode portions with respect to the attachment belt is not displaced. However, when the attachment belt is stretched/contracted along an extending direction so as to follow the movement of the wearer, the positions of the electrode portions are displaced so as to follow the stretching/contracting movement of the attachment belt. Accordingly, there is a problem that contact positions of the electrode portions with respect to the biological surface are not stable, which hinders good detection of an electrocardiographic signal. There is also a danger of disconnection and so on as the wires of the electrode portions are pulled along the extending direction of the attachment belt due to the stretching/contracting movement of the attachment belt.

SUMMARY OF THE INVENTION

The present invention has been made in view of the above circumstances and an object of the present invention is to provide a biological information detecting device capable of stably detecting a biological signal in good condition.

In order to solve the above problems, there is provided a biological information detecting device of the invention including a device body, a pair of electrode portions provided in the device body and respectively contacting a biological surface, a band-shaped fixing member for covering the pair of electrode portions and fixing the device body to a body and a guide portion arranged between each of the electrode portions and the fixing member, which allows relative movement between each of the electrode portions and the fixing member in an extending direction of the fixing member and restricts movement in a width direction orthogonal to the extending direction.

According to the structure, as the guide portion allowing relative movement between each of the electrode portions and the fixing member in the extending direction and restricting movement in the width direction is provided, for example, when the fixing member is stretched/contracted along the extending direction due to deep breath or movement of the wearer, each of the electrode portions and the fixing member relatively move along the extending direction through the guide portion. That is, the electrode portions do not follow the stretch/contraction and so on of the fixing member, therefore, it is possible to restrain the electrode portions from being pulled in the extending direction with the stretch/contraction of the fixing member. Therefore, it is possible to suppress the displacement of positions of the electrode portions with respect to the wearer, which stabilize a contact state and contact positions of the electrode portions with respect to the wearer.

As it is also possible to restrain the electrode portions from being pulled in the extending direction with the stretch/contraction of the fixing member, disconnection and the like of the electrode portions can be also prevented.

On the other hand, as relative movement between each of the electrode portions and the fixing member in the width direction is restricted by the guide portion, it is possible to prevent the electrode portions from being displaced or removed with respect to the fixing member in the width direction, which stabilize the contact state and contact positions of the electrode portions with respect to the wearer.

The guide portion may include an engaging portion arranged in the electrode portion's side, and an engaged portion arranged in the fixing member's side, with which the engaging portion is engaged in the width direction.

According to the structure, as the engaging portion and the engaged portion are engaged in the width direction, an engagement state between each of the electrode portions and the fixing member by the guide portion can be positively maintained in a state where the relative movement between each of the electrode portions and the fixing member in the extending direction is allowed and the movement in the width direction is restricted.

Plural lines of the engaging portions and engaged portions are arranged along the width direction.

According to the structure, as plural engaging portions and engaged portions are formed in the width direction, even when the engaging portion is relatively displaced with respect to one engaged portion in the width direction and climbs over one engaged portion by any chance due to violent movement (for example, twisting and so on) by the wearer, the engagement state between the engaging portion and the engaged portion is maintained as the engaging portion is engaged again with another engaged portion adjacent to one engaged portion. Accordingly, the contact state and contact positions of the electrode portions with respect to the wearer can be positively stabilized.

A length of the engaging portion extending along the extending direction may be longer than a length of the engaged portion along the extending direction.

According to the structure, as the length of the engaging portion in the electrode portion's side in the extending direction is longer than the engaged portion in the fixing member's side in the extending direction, it is possible to suppress the protrusion of the engaged portion from outer end portions of the electrode portions in the extending direction. Therefore, it is possible to prevent the engaged portion from contacting with the biological surface of the wearer, which realizes comfortable wearing feeling.

The guide portion may include an engaging portion arranged in one member of the electrode portion and the fixing member as well as engaged with the other member in the width direction.

According to the structure, as the engaging portion in one member is engaged with the other member in the width direction, the other member itself can be functioned as the guide portion. Accordingly, simplification of the structure and cost reduction can be realized.

According to the present invention, a biological signal can be stably detected in good condition.

DETAILED DESCRIPTION OF THE PREFERRED EMBODIMENTS

First Embodiment

Next, a first embodiment of the present invention will be explained with reference to the drawings.

Figure 1:
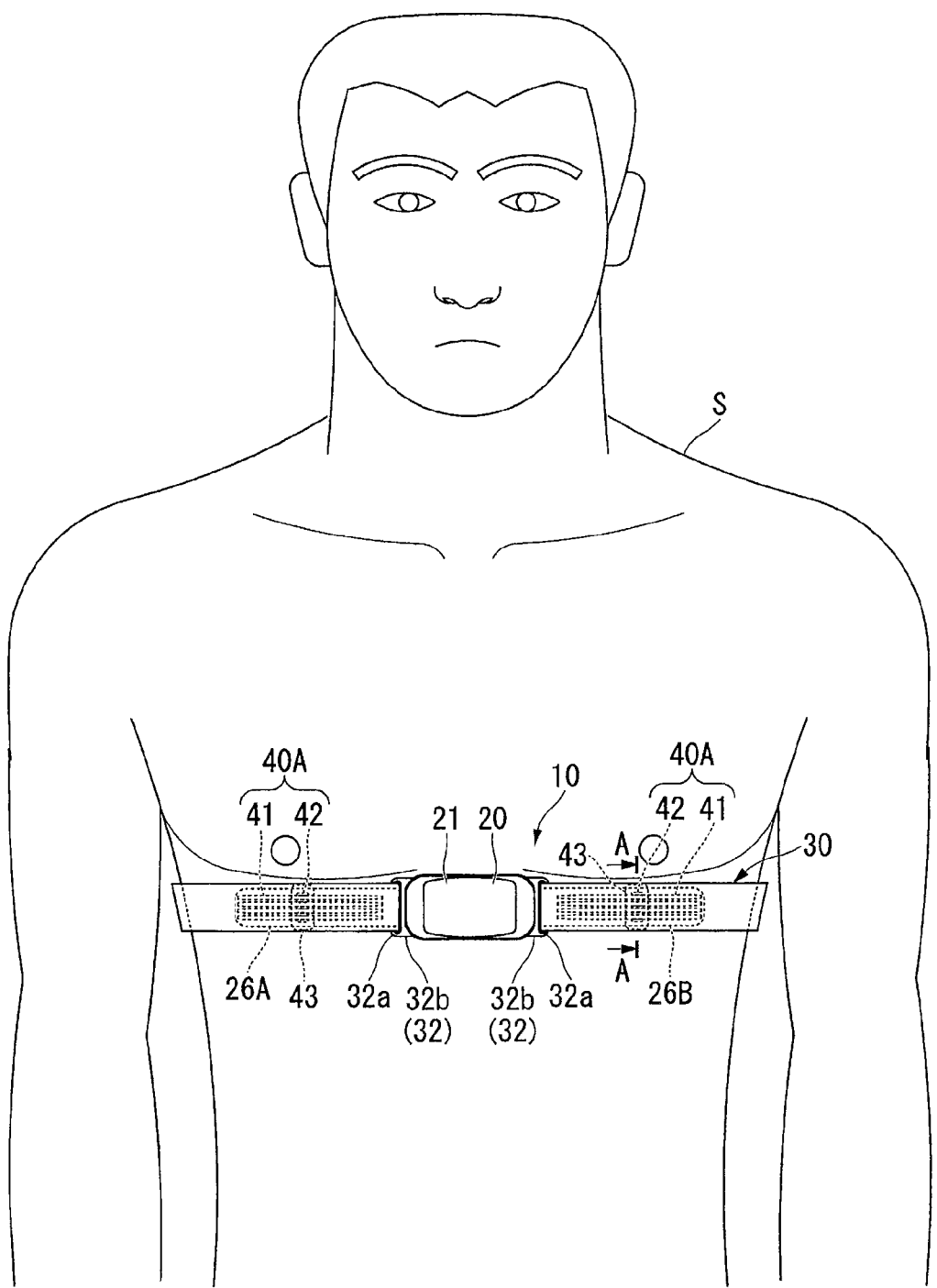
FIG. 1 is a front view showing a state where a heart rate measuring device as a biological information detecting device according to a first embodiment of the present invention is attached to a wearer.

FIG. 1 is a front view showing a state where a heart rate measuring device 10 as a biological information detecting device according to the first embodiment of the present invention is attached to a wearer S.

As shown in FIG. 1, the heart rate measuring device (biological information detecting device) 10 detects an electrocardiographic signal generated by heartbeats by being attached to a chest as a biological surface of the wearer S and transmits the detected electrocardiographic signal by wireless communication.

Figure 2:
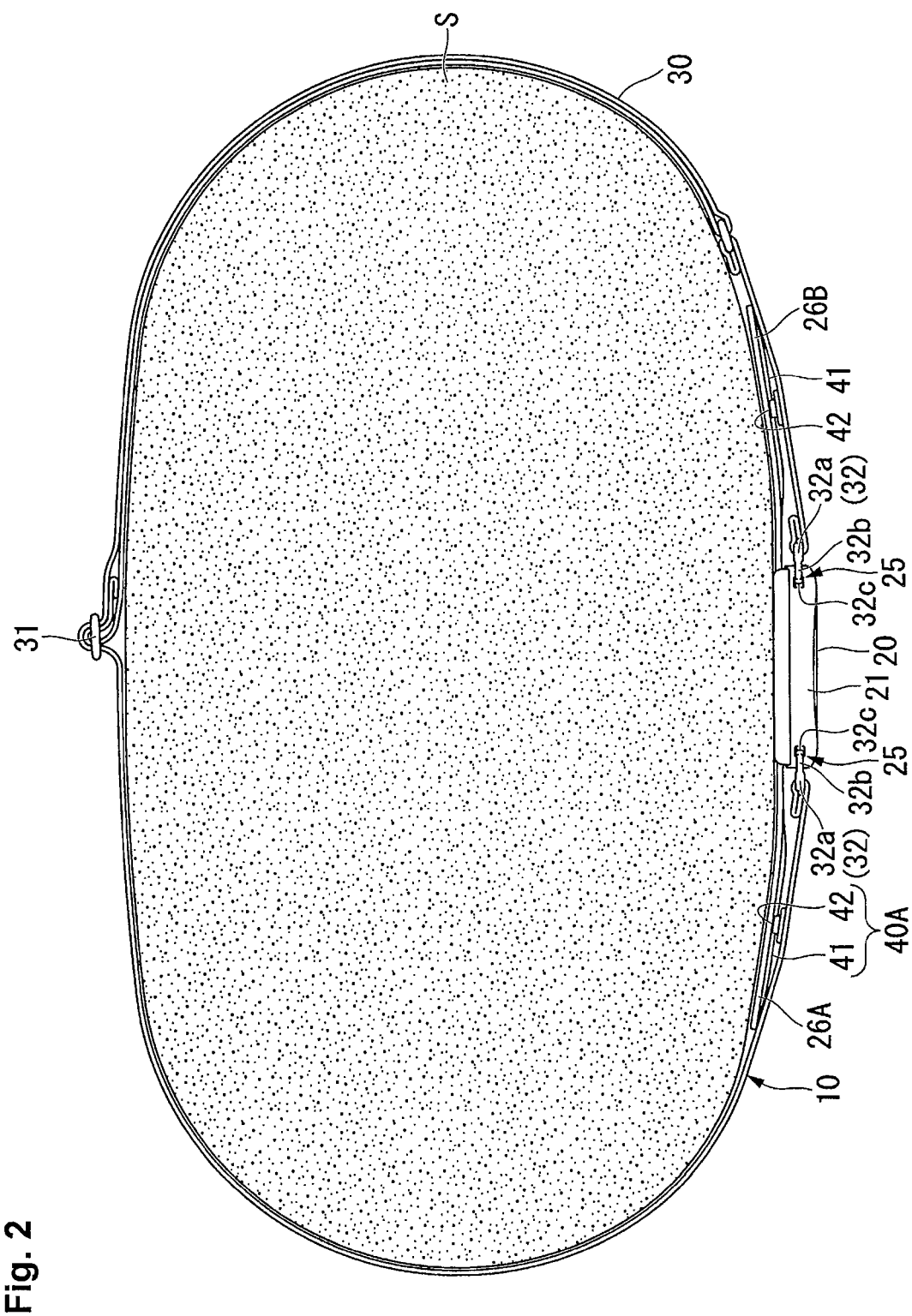
FIG. 2 is a transverse sectional view showing a state where the heart rate measuring device is attached to the wearer.
Figure 3:
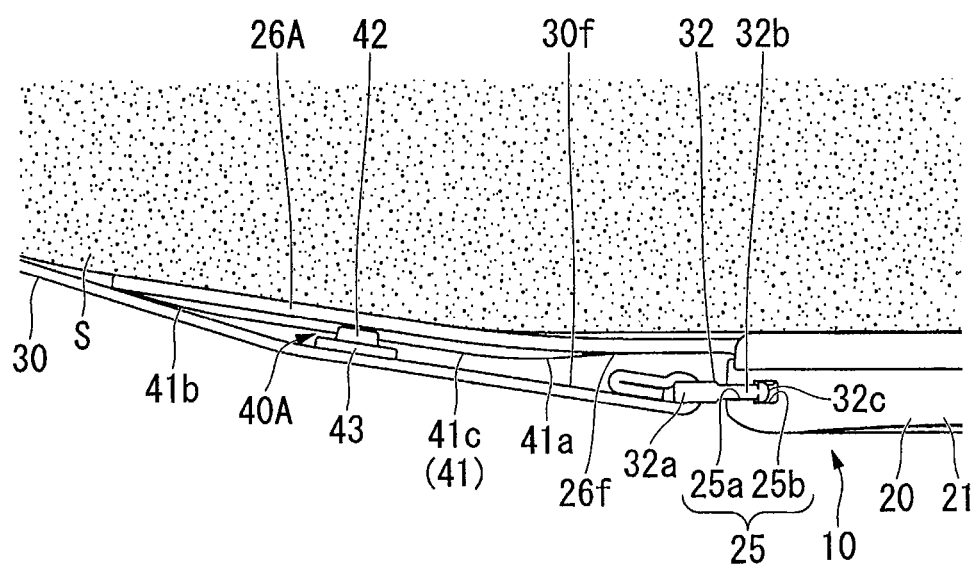
FIG. 3 is an enlarged view of a relevant part of FIG. 2.
Figure 4:
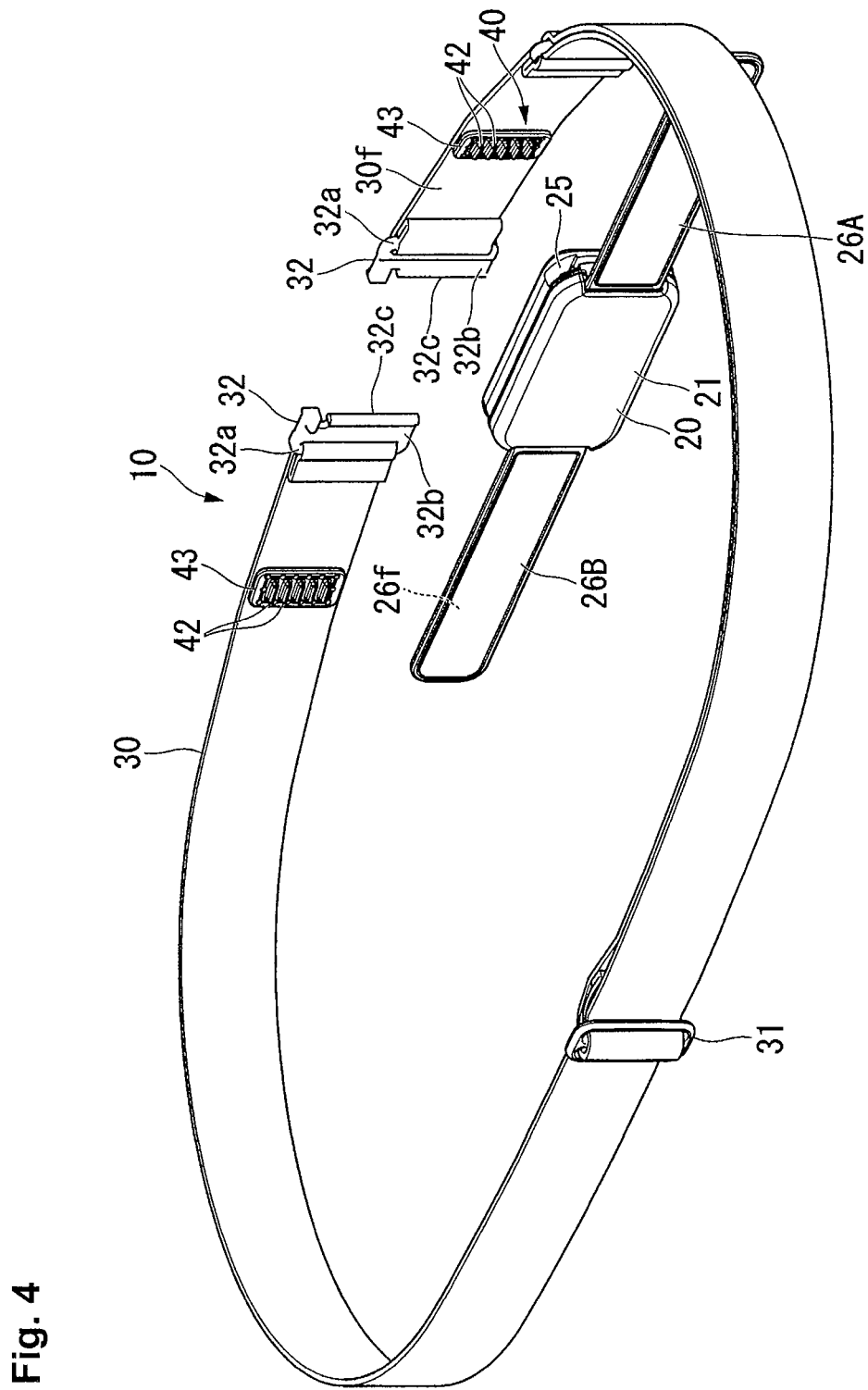
FIG. 4 is an exploded perspective view showing a structure of the heart rate measuring device.

FIG. 2 is a transverse sectional view showing a state where the heart rate measuring device 10 is attached to the wearer S. FIG. 3 is an enlarged view of a relevant part of FIG. 2. FIG. 4 is an exploded perspective view showing the heart rate measuring device 10.

As shown in FIG. 1 to FIG. 4, the heart rate measuring device 10 includes a device body 20, a pair of electrode portions 26A, 26B integrally provided at both ends of the device body 20 and a fixing band 30 for attaching the device body 20 to the chest of the wearer S.

The device body 20 includes a case 21 formed in a rectangular shape in planar view and a not-shown detection circuit substrate provided inside the case 21.

As shown in FIG. 3, locking grooves 25 for connecting the fixing band 30 are provided so as to extend along the short side direction of the case 21 at both end portions in the longitudinal direction of the case 21. Each locking groove 25 includes an opening 25a opening toward the outside in the longitudinal direction of the case 21. In a bottom side of each locking groove 25, a widened portion 25b a groove width of which is increased to be larger than the opening 25a side is formed.

The detection circuit substrate includes a transmission circuit generating an electric signal based on a signal detected by the pair of electrode portions 26A and 26B and a wireless transmission portion (both are not shown) transmitting the electric signal generated in the transmission circuit to the outside.

Each of the electrode portions 26A and 26B is formed by a band-shaped conductive elastomer. As the conductive elastomer, for example, conductive silicon rubber in which carbon black is blended, conductive rubber in which carbon black is blended, conductive polyurethane rubber in which carbon black is blended and so on can be used.

As shown in FIG. 4, the respective electrode portions 26A and 26B are arranged in both sides interposing the device body 20 therebetween. The respective electrode portions 26A and 26B are connected to the case 21 so that connecting portions 27A and 27B (refer to FIG. 5) formed in one end portions in the longitudinal direction thereof are housed inside the case 21. The electrode portions 26A and 26B are electrically connected to the detection circuit substrate in the case 21 through not-shown wiring patterns.

Accordingly, a signal detected by the electrode portions 26A and 26B is outputted to the detection circuit substrate.

In the above device body 20, an electrocardiographic signal generated by heartbeats is detected by the pair of electrode portions 26A and 26B. The not-shown detection circuit substrate of the device body 20 outputs the electrocardiographic signal detected by the pair of electrode portions 26A and 26B to the outside by wireless communication.

The fixing band (fixing member) 30 is an elastic strap having ends which is formed in a band shape, and the device body 20 is connected so as to extend between both end portions provided along the extending direction of the fixing band 30. Accordingly, the heat rate measuring device 10 is attached so as to surround the chest of the wearer S over the whole circumference.

In the center part in the extending direction of the fixing band 30 (portion positioned in the back side of the wearer S), a length adjusting member 31 for adjusting the length of the fixing band 30 is provided.

In the both end portions in the extending direction of the fixing band 30, strap attaching/detaching members 32 for enabling attachment/detachment between the fixing band 30 and the device body 20 are provided. Each strap attaching/detaching member 32 includes a frame body 32a having an oval ring shape, a plate portion 32b continuously formed in one end portion extending along the short-axis direction of the frame body 32a and a hook portion 32c continuously provided along the long-axis direction of the frame body 32a at an end portion opposite to the frame body 32a in the plate portion 32b. A plate thickness of the hook portion 32c is formed to be thicker than that of the plate portion 32b. The frame body 32a, the plate portion 32b and the hook portion 32c may be integrally formed as well as may be bonded to each other after being formed separately.

The strap attaching/detaching members 32 formed as described above are attached to the fixing band 30 in a manner described below. That is, after an end portion of the fixing band 30 is inserted into the frame body 32a of the strap attaching/detaching member 32, the end portion is turned to the opposite side of the hook portion 32c and fixed to the fixing band 30 itself. Accordingly, the strap attaching/detaching members 32 are attached to both ends in the longitudinal direction of the fixing band 30.

Then, when the fixing band 30 is attached to the device body 20, the plate portion 32b and the hook portion 32c of the strap attaching/detaching member 32 is inserted into the locking groove 25 of the case 21 from one end side in the short side direction of the case 21 as shown in FIG. 3. Then, the hook portion 32c in the strap attaching/detaching member 32 is locked in the widened portion 25b of the locking groove 25 in the state where the plate portion 32b is inserted into the opening 25a of the locking groove 25. The fixing band 30 is attached to the device body 20 by locking the strap attaching/detaching members 32 in the manner described above.

As shown in FIG. 2 and FIG. 3, the electrode portions 26A and 26B are covered with the fixing band 30 in the state where the fixing band 30 is attached to the device body 20. That is, the fixing band 30 has a function of fixing the device body 20, the electrode portions 26A and 26B to the body of the wearer S so as to be attached/detached and a function of maintaining a contact state between the chest and the electrode portions 26A, 26B by covering the electrode portions 26A and 26B from the outside and pressing the electrode portions 26A and 26B to the chest of the wearer S when the heart rate measuring device 10 is attached to the wearer S.

Figure 5:
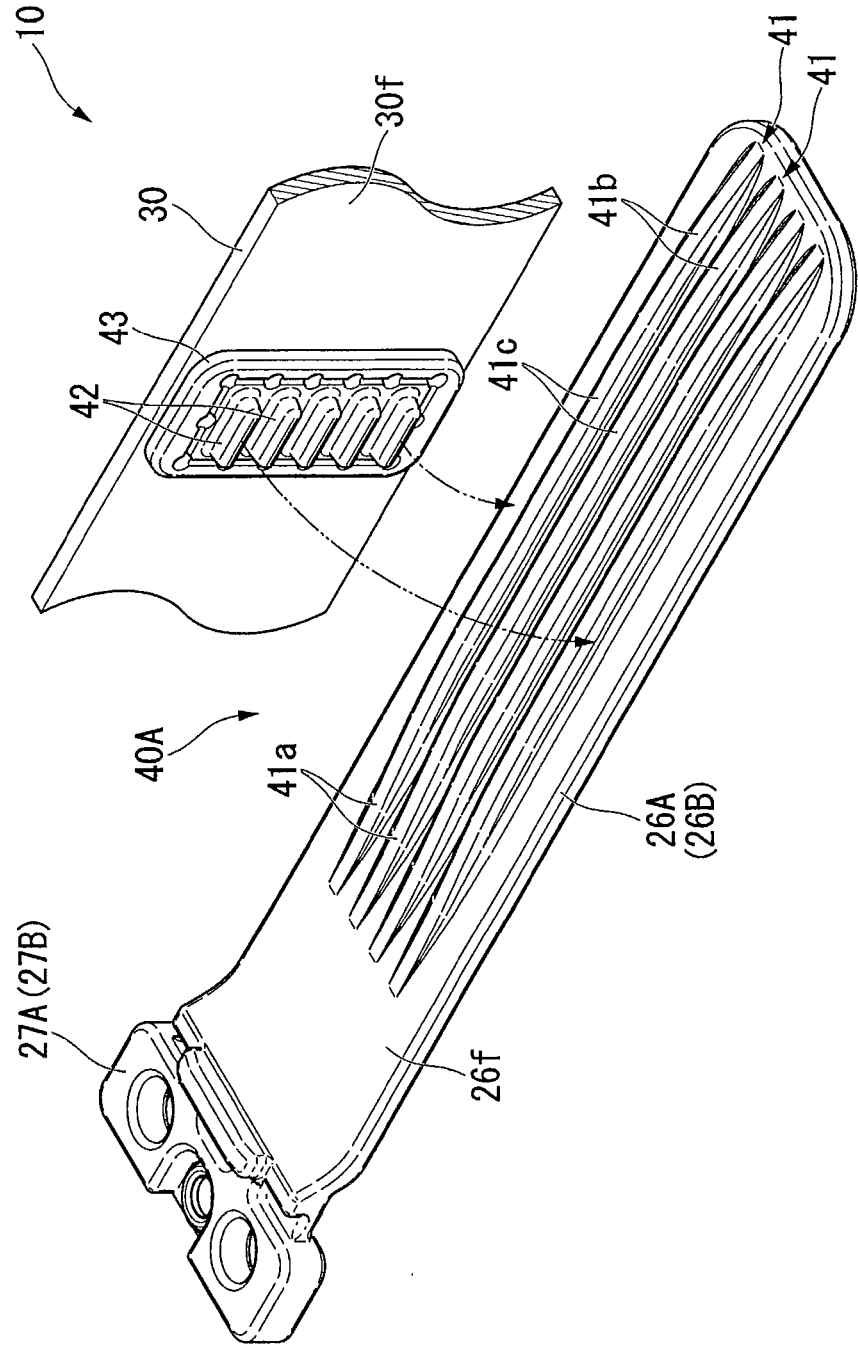
FIG. 5 is a perspective view showing a guide portion in the heart rate measuring device.
Figure 6:
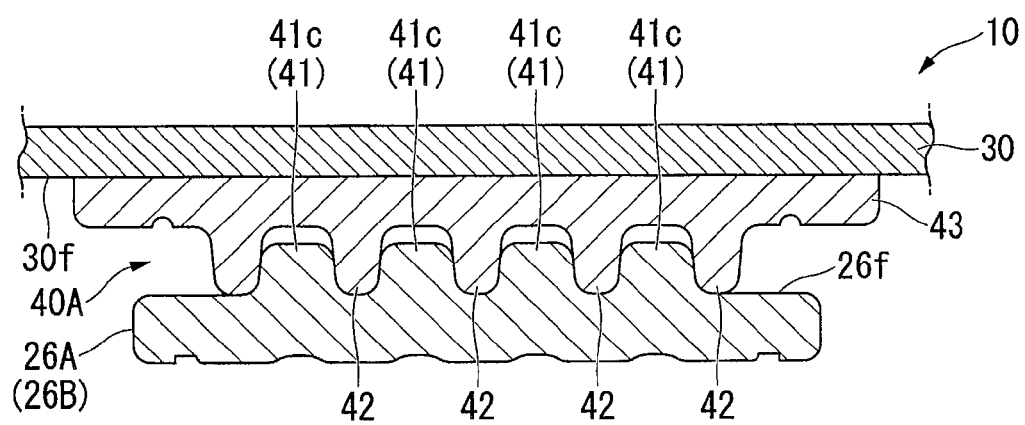
FIG. 6 is a cross-sectional view taken along A-A line of FIG. 1.

FIG. 5 is a perspective view showing a guide portion 40A in the heart rate measuring device 10. FIG. 6 is a cross-sectional view corresponding to A-A line of FIG. 1.

As shown in FIG. 5 and FIG. 6, the guide portions 40A allowing relative movement of the electrode portions 26A, 26B and the fixing band 30 in the extending direction of the fixing band 30 (hereinafter referred to merely as the extending direction) and restricting movement in a width direction orthogonal to the extending direction (hereinafter referred to merely as the width direction) are arranged between the electrode portions 26A, 26B and the fixing band 30.

In the embodiment, each guide portion 40A includes rail-shaped protruding ridges (engaging portion) 41 extending continuously along the extending direction in the electrode portions 26A/26B side and convex portions (engaged portion) 42 arranged in the fixing band 30 side and fitted to the protruding ridges 41 in the width direction.

The protruding ridges 41 are integrally formed with each of the electrode portions 26A and 26B on a surface 26f positioned in the fixing band 30 side in each of the electrode portions 26A and 26B. Plural lines of the protruding ridges 41 (for example, four lines in the embodiment) are formed along the width direction at equal intervals on the surface 26f of each of the electrode portions 26A and 26B. Each protruding ridge 41 includes a central extending portion 41c positioned at the central part in the extending direction and slope portions 41a and 41b continuously formed at both end portions positioned along the extending direction of the central extending portion 41c, the protruding height of which from the surface 26f of each of the electrode portions 26A and 26B is gradually reduced toward the outside along the extending direction. The protruding height of the central extending portion 41c from the surface 26f of each of the electrode portions 26A and 26B is uniform over the whole portion along the extending direction.

A cross-sectional shape seen from the extending direction of each protruding ridge 41 is a trapezoid shape the width of which is gradually reduced from a base end portion toward a tip portion. That is, both end sides of each protruding ridge 41 positioned in both sides in the width direction are inclined with respect to a normal line direction of the surface 26f of each of the electrode portions 26A and 26B.

The convex portions 42 are integrally formed with a rectangular base member 43 provided in a surface 30f positioned in the electrode portions 26A/26B side in the fixing band 30.

The base member 43 is sewed to the fixing band 30 in a state where the longitudinal direction of the base member 43 corresponds to the width direction of the fixing band 30. It is also preferable that the base member 43 is fixed to the fixing band 30 by adhesion and the like.

The convex portions 42 are formed in a rail shape continuously extending along the extending direction in the base member 43. A length of the convex portions 42 in the extending direction is shorter than a length of the protruding ridges 41 in the extending direction. Plural lines of convex portions 42 are formed along the width direction at equal intervals. The number of the formed respective convex portions 42 is one larger than the number of the protruding ridges 41 (five lines in the embodiment) so as to be positioned in both sides in the width direction of the respective protruding ridges 41. Then, the above protruding ridges 41 are respectively fitted between respective convex portions 42 adjacent to one another in the width direction. That is, the protruding ridges 41 are sandwiched between respective convex portions 42 in the width direction as shown in FIG. 6.

The cross-sectional shape of each convex portion 42 seen from the extending direction is the trapezoid shape the width of which is gradually reduced from the base end portion toward the tip portion. Moreover, the respective convex portions 42 are inclined with respect to a normal line direction of the surface 30f of the fixing band 30 so that both side surfaces positioned in both sides in the width direction are parallel to both side surfaces of the protruding ridges 41.

The protruding height of the respective convex portions 42 protruding along the normal line direction of the surface 30f of the fixing band 30 is larger than the protruding height protruding along the normal line direction of the surface 26f of each of the electrode portions 26A and 26B in the protruding ridges 41. Therefore, gaps are formed between tip portions of the protruding ridges 41 and the base member 43 in the state shown in FIG. 6.

When the fixing band 30 is attached to the device body 20 under the above structure, the heart rate measuring device 10 is attached to the chest of the wearer S in the state where the protruding ridges 41 in the electrode portion 26A/26B side are respectively fitted between respective convex portions 42 in the fixing band 30 side. Accordingly, the heart rate measuring device 10 is attached to the wearer S in the state where the electrode portions 26A and 26B are covered with the fixing band 30 from the outside. At this time, portions where the convex portions 42 are fitted to the protruding ridges 41 in the electrode portions 26A and 26B are pressed onto the chest side of the wearer S more locally than other portions. That is, a fastening force of the fixing band 30 is locally transmitted to the electrode portions 26A and 26B through the convex portions 42. Accordingly, the electrode portions 26A and 26B are allowed to contact the chest positively, which enables positive detection of the electrocardiographic signal.

As the protruding ridges 41 and the convex portions 42 of the guide portions 40A are fitted to each other in the width direction in the embodiment, relative movement in the extending direction between the electrode portions 26A/26B and the fixing band 30 is allowed as well as movement in the width direction is restricted.

Specifically, when the fixing band 30 is stretched/contracted in the extending direction due to deep breath or movement of the wearer S, the protruding ridges 41 and the convex portions 42 relatively slide along the extending direction, as a result, the electrode portions 26A/26B and the fixing band 30 are relatively moved along the extending direction. That is, the electrode portions 26A and 26B do not follow the stretch/contraction of the fixing band 30, therefore, it is possible to restrain the electrode portions 26A and 26B from being pulled in the extending direction with the stretch/contraction of the fixing band 30. Therefore, it is possible to suppress the displacement of positions of the electrode portions 26A and 26B with respect to the chest of the wearer S and to stabilize the contact state and contact positions of the electrode portions 26A and 26B with respect to the chest.

As it is possible to restrain the electrode portions 26A and 26B from being pulled in the extending direction with the stretch/contraction of the fixing band 30, it is also possible to prevent disconnection and so on in the electrode portions 26A and 26B.

On the other hand, as the protruding ridges 41 and the convex portions 42 of the guide portion 40A are fitted to each other in the width direction, movement between the electrode portions 26A/26B and the fixing band 30 in the width direction can be restricted. Accordingly, it is possible to prevent the electrode portions 26A and 26B from being displaced or removed with respect to the fixing band 30 in the width direction, thereby stabilizing the contact state and the contact positions of the electrode portions 26A and 26B with respect to the chest.

Consequently, it is possible to stably detect an electrocardiographic signal in good condition by the electrode portions 26A and 26B.

Additionally, as the protruding ridges 41 and the convex portions 42 are fitted to each other in the width direction in the embodiment, the fitted state between the electrode portions 26A/26B and the fixing band 30 by the guide portion 40A can be positively maintained under the condition that the relative movement between the electrode portions 26A/26B and the fixing band 30 in the extending direction is allowed and the movement in the width direction is restricted.

Furthermore, plural protruding ridges 41 and convex portions 42 are arranged in the width direction in the embodiment, therefore, even when the convex portion 42 is relatively displaced with respect to one protruding ridge 41 in the width direction and climbs over one protruding ridge 41 by any chance due to violent movement (for example, twisting and so on) by the wearer S, the fitted state between the protruding ridges 41 and the convex portions 42 is maintained as another protruding ridge 41 adjacent to one protruding ridge 41 is fitted to the convex portion 42 again. Accordingly, the contact state and the contact positions of the electrode portions 26A and 26B with respect to the chest can be positively stabilized.

Moreover, as the length of the convex portions 42 in the fixing band 30 side along the extending direction is shorter than the length of the protruding ridges 41 in the electrode portions 26A/26B side along the extending direction, it is possible to suppress the protrusion of the convex portions 42 from the outer end portions in the extending direction of the electrode portions 26A/26B. Accordingly, the contact of the convex portions 42 with respect to the biological surface can be suppressed and comfortable wearing feeling can be realized.

Additionally, as the slope portions 41a and 41b the protruding height of which is gradually reduced toward the outside along the extending direction are formed in both end portions in the extending direction of the central extending portion 41c of the protruding ridges 41, a fitting force between the protruding ridges 41 and the convex portions 42 is increased toward the central extending portion 41c through the slope portions 41a and 41b. Therefore, for example, when the protruding ridges 41 are fitted to the convex portions 42, the electrode portions 26A/26B and the fixing band 30 are relatively moved in the extending direction and the convex portions 42 are inserted into the protruding ridges 41 from the slope portions 41a/41b side, thereby fitting the protruding ridges 41 to the convex portions 42 easily.

Modification Example of First Embodiment

Figure 7:
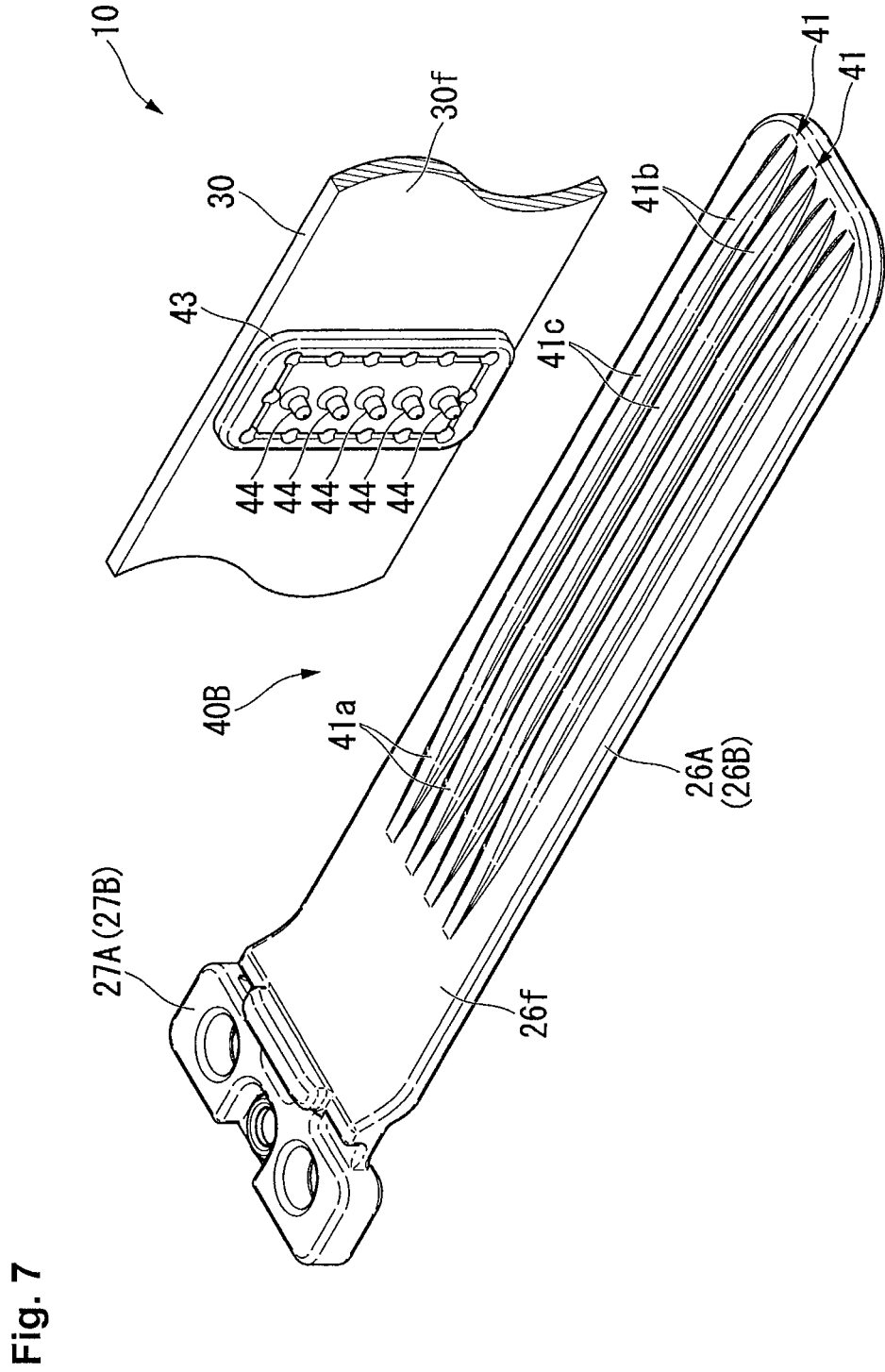
FIG. 7 is a view showing a modification example of the first embodiment, which is a perspective view corresponding to FIG. 5.

Next, a modification example of the above first embodiment will be shown. In the first embodiment, the case where the convex portions 42 in the fixing band 30 side have the rail shape extending along the extending direction has been explained, however, the present invention is not limited to this. For example, convex portions (engaged portions) 44 may have a cylindrical shape extending toward the electrode portions 26A/26B side (the normal line direction of the surface 30f of the fixing band 30) as a guide portion 40B shown in FIG. 7.

According to the structure, the same operation and effect as the first embodiment can be obtained as well as the contact area between the protruding ridges 41 and the convex portions 44 along the extending direction can be reduced to be smaller than the rail-shaped convex portions 42 as in the first embodiment at the time of fitting the protruding ridges 41 to the convex portions 44. Accordingly, the fitting force between the protruding ridges 41 and the convex portions 44 can be reduced, and the protruding ridged 41 can be easily fitted between respective convex portions 44, which facilitates attachment work. When the fixing band 30 is stretched/contracted in the extending direction, it is possible to allow the electrode portions 26A/26B and the fixing band 30 to relatively move along the extending direction smoothly.

Figure 8:
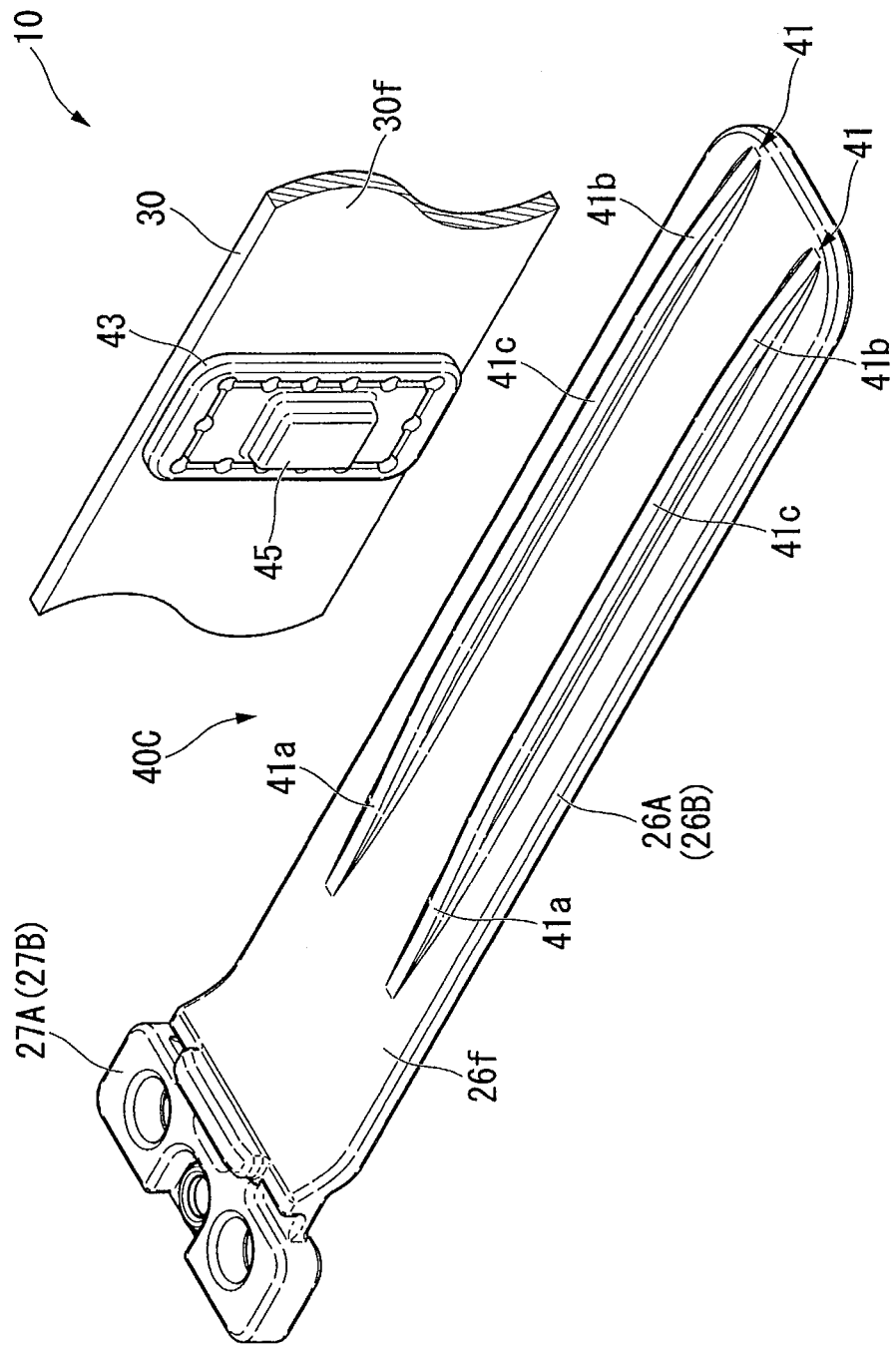
FIG. 8 is a view showing a modification example of the first embodiment, which is a perspective view corresponding to FIG. 5.

In a guide portion 40C shown in FIG. 8, the protruding ridges 41 have a rail shape continuously extending along the extending direction, and a pair of protruding ridges 41 are arranged at both end portions in the width direction of each of the electrode portions 26A and 26B. On the other hand, a convex portion (engaged portion) 45 has a rectangular block shape arranged along the width direction in the fixing band 30 at a portion positioned between respective protruding ridges 41. When the fixing band 30 is attached to the device body 20, the convex portion 45 is fitted between the respective protruding ridges 41 in the width direction.

According to the structure, the same operation and effect as the first embodiment can be obtained as well as attachment work can be easily performed only by fitting one convex portion 45 between the respective protruding ridges 41. Moreover, when the fixing band 30 is stretched/contracted in the extending direction, it is possible to relatively move the electrode portions 26A, 26B and the fixing band 30 in the extending direction smoothly.

Figure 9:
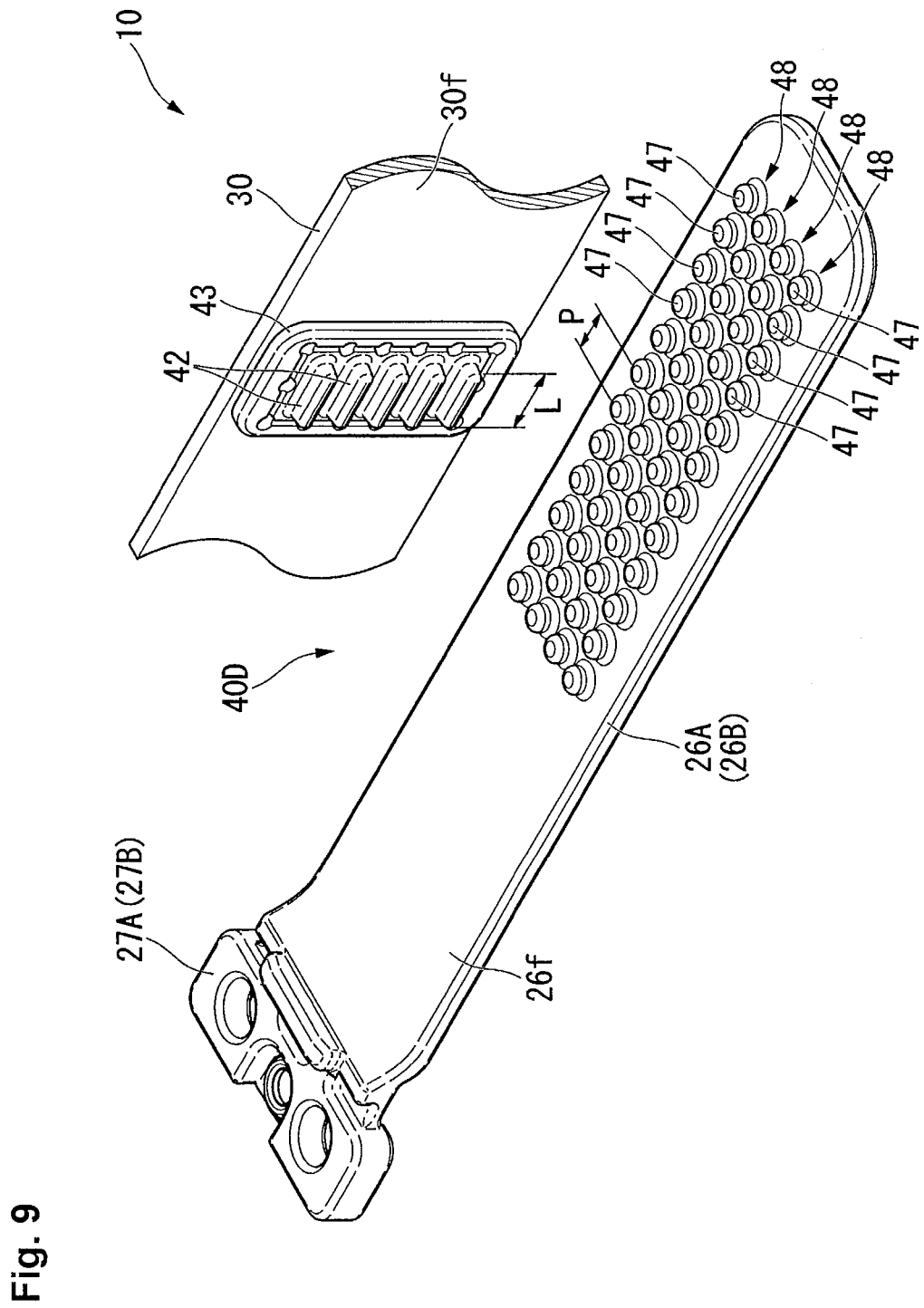
FIG. 9 is a view showing a modification example of the first embodiment, which is a perspective view corresponding to FIG. 5.

A guide portion 40D shown in FIG. 9 has cylindrical protrusions 47 protruding toward the fixing band 30 side (the normal line direction of the surface 26f) in each of the electrode portions 26A and 26B. Plural protrusions 47 are arranged at intervals along the extending direction to form protrusion lines (engaging portions) 48, and plural protrusion lines 48 (for example, four lines in the embodiment) are arranged at intervals in the width direction. An arrangement pitch P between the protrusions 47 formed along the extending direction is preferably smaller than a length L of the convex portions 42 in the extending direction.

According to the structure, the same operation and effect as the above embodiment can be obtained.

Furthermore, the case where the protruding ridges 41 or the protrusion lines 48 are arranged in the electrode portions 26A/26B side has been explained in the first embodiment and respective modification examples, however, the present invention is not limited to this. For example, grooves and so on to be fitted to the convex portions 42, 44 and 45 may be formed in the electrode portions 26A/26B side.

Though the case where the protruding ridges 41 or protrusion lines 48 are arranged in the electrode portions 26A/26B side and the convex portions 42, 44 and 45 are arranged in the fixing band 30 side has been explained in the above first embodiment and respective modification examples, it is also preferable that the protruding ridges 41 and protrusion lines 48 are arranged in the fixing band 30 side and the convex portions 42, 44 and 45 are arranged in the electrode portions 26A/26B side, which is converse to the above.

It is further preferable to appropriately perform design change concerning fitting positions between the protruding ridges 41 or the protruding lines 48 and the respective convex portions 42, 44 and 45 along the extending direction.

Second Embodiment

Figure 10:
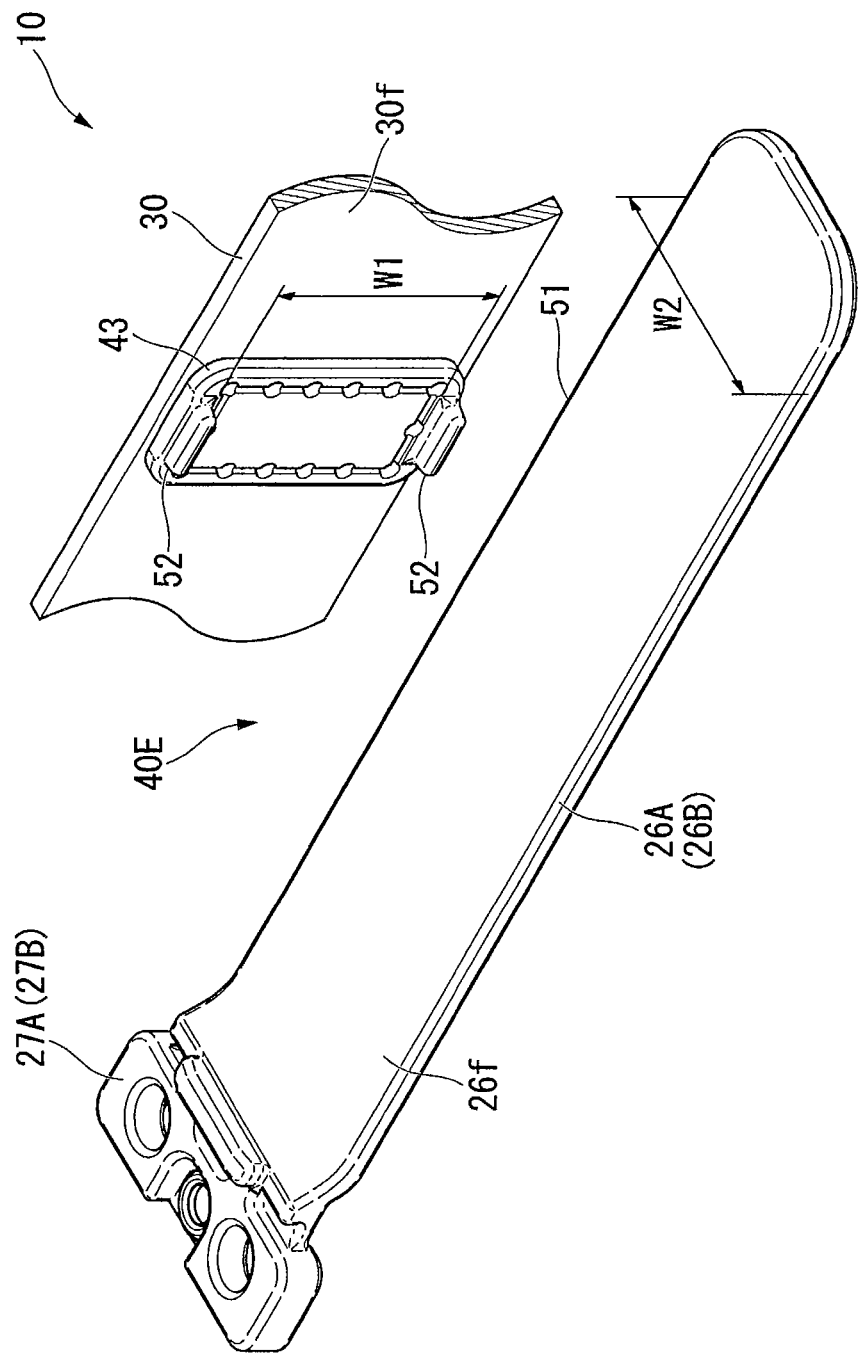
FIG. 10 is a view showing a second embodiment, which is a perspective view corresponding to FIG. 5.

Next, a second embodiment of the heart rate measuring device 10 according to the present invention will be explained. In the following explanation, the same components as the first embodiment are denoted by the same numerals and signs and explanation thereof is omitted. FIG. 10 is a view showing a structure of a guide portion 40E according to a second embodiment of the present invention. The present embodiment differs from the first embodiment in a point that edge portions in the width direction of each of the electrode portions (the other member) 26A and 26B are used as the guide portion 40E as shown in FIG. 10.

Specifically, the guide portion 40E according to the embodiment includes a pair of convex portions (engaging portions) 52 in the fixing band (fixing member, one member) 30, which protrude toward the electrode portions 26A/26B. These convex portions 52 have a rail shape continuously extending along the extending direction. A width W1 between respective convex portions 52 along the width direction is equivalent to a width W2 of each of the electrode portions 26A and 26B, and each of the electrode portions 26A and 26B is fitted to the inside of respective convex portions 52.

According to the structure, as each of the electrode portions 26A and 26B itself is fitted between respective convex portions 52 in the width direction, relative movement between the electrode portions 26A/26B and the fixing band 30 in the extending direction is allowed and movement in the width direction is restricted.

The same operation and effect as the first embodiment can be obtained in the embodiment as well as simplification in structure and cost reduction can be realized by allowing each of the electrode portions 26A and 26B itself to function as the guide portion 40E.

The present invention is not limited to the above respective embodiments explained with reference to the drawings but various modification examples can be considered within a technical scope thereof.

For example, the structure in which the engaging portions (for example, the protruding ridges 41, the protrusion lines 48 and the electrode portions 26A and 26B themselves) in the electrode portions 26A/26B side are fitted to the engaged portions (for example, the convex portions 42, 44, 45 and 52) in the fixing band 30 has been explained in respective embodiments, however, the present invention is not limited to this. That is, it is sufficient that the guide portion has the structure which allows relative movement between the electrode portions 26A/26B and the fixing band 30 in the extending direction and restricts movement in the width direction.

In particular, it is sufficient that the engaging portions and the engaged portions are engaged with each other. For example, the engaging portions may be engaged to the engaged portion with a gap in the width direction. An engaging force between the engaging portions and the engaged portions can be adjusted by appropriately adjusting the number, the height, the width, the length along the extending direction and so on of the engaging portions and the engaged portions.

The width of the protruding ridges 41 and so on can be changed along the extending direction. Accordingly, the engaging force between the engaging portion and the engaged portion can be changed in the extending direction.

Though the structure in which the convex portions 42, 44 and 45 are attached to the fixing band 30 through the base member 43 has been explained in the above embodiments, the present invention is not limited to this. It is also preferable that the convex portions 42, 44 and 45 are directly formed on the fixing band 30.

Additionally, the heart rate measuring device 10 which measures the heart rate of the wearer S has been explained in the above embodiments as the biological information detecting device according to the present invention, however, the present invention is not limited to this and can be applied to various types of biological information detecting device. That is, the structure of the present invention can be applied to devices measuring blood pressure, body temperature, muscle potential and so on as biological information detecting devices.

The case where the fixing member is made of the material having elasticity has been explained in the above embodiments, however, the present invention is not limited to this, and various materials can be applied.

Also in the embodiments, the fixing member has been explained as the fixing band 30 having ends, however, the present invention is not limited to this, and a structure in which all the device body 20, the electrode portions 26A and 26B are covered from the outside by using a fixing band with no end.

It is also preferable to apply a structure in which a band-shaped fixing member is provided at garments (which can be worn by the body such as a shirt, pants and a hat).

Furthermore, the case where both edges in the width direction of each of the electrode portions 26A and 26B are used as the guide portion 40E has been explained in the above second embodiment, however, the present invention is not limited to this, and the fixing band 30 itself can be used as the guide portion.

Other components in the above embodiments can be appropriately replaced with well-known components within a scope not departing from the gist of the present invention.

What is claimed is:

1. A biological information detecting device comprising:
   a device body;
   a pair of electrode portions in the device body and respectively adapted to contact a biological surface;
   a band-shaped fixing member that covers the pair of electrode portions and is adapted to fix the device body to the biological surface; and
   a guide portion between each of the electrode portions and the fixing member that allows relative movement between each of the electrode portions and the fixing member in an extending direction of the fixing member and restricts movement in a width direction orthogonal to the extending direction,
   the guide portion having a base portion attached to the fixing member.

2. The biological information detecting device according to claim 1, wherein the guide portion includes an engaging portion on a same side as the electrode portions, and an engaged portion extending from the base portion, with which the engaging portion is engaged in the width direction.

3. The biological information detecting device according to claim 2, wherein a plurality of the engaging portions and engaged portions reside along the width direction.

4. The biological information detecting device according to claim 2, wherein a length of the engaging portion extending in the extending direction is longer than a length of the engaged portion in the extending direction.

5. The biological information detecting device according to claim 1, wherein the guide portion includes an engaging portion at a first side of the electrode portion and the fixing member and at a second side of the electrode portion and the fixing member in the width direction.

* * * * *